(12) United States Patent
Richelsoph

(10) Patent No.: US 8,870,923 B2
(45) Date of Patent: Oct. 28, 2014

(54) ROD TO ROD CONNECTOR WITH LOAD SHARING

(76) Inventor: Marc E. Richelsoph, Charlotte, NC (US)

( * ) Notice: Subject to any disclaimer, the term of this patent is extended or adjusted under 35 U.S.C. 154(b) by 107 days.

(21) Appl. No.: 12/613,852

(22) Filed: Nov. 6, 2009

(65) Prior Publication Data
US 2011/0110712 A1    May 12, 2011

(51) Int. Cl.
*A61B 17/70*    (2006.01)

(52) U.S. Cl.
CPC .................. *A61B 17/7052* (2013.01)
USPC ..... 606/252; 403/290; 403/109.1; 403/109.4; 606/258; 606/259

(58) Field of Classification Search
CPC .. A61B 17/7052; A61B 17/7032; F16B 2/06; F16B 7/1463
USPC ........................ 403/290, 109.1, 109.4, 305; 606/250–253, 278, 258–259
See application file for complete search history.

(56) References Cited

U.S. PATENT DOCUMENTS

| | | | |
|---|---|---|---|
| 5,575,790 A * | 11/1996 | Chen et al. ...................... 606/60 |
| 6,110,173 A * | 8/2000 | Thomas, Jr. .................. 606/252 |
| 6,306,137 B2 * | 10/2001 | Troxell .......................... 606/252 |
| 6,328,740 B1 * | 12/2001 | Richelsoph .................... 606/252 |
| 6,355,040 B1 * | 3/2002 | Richelsoph et al. ........... 606/272 |
| 6,866,664 B2 * | 3/2005 | Sch.ang.r et al. ............. 606/252 |
| 6,875,211 B2 * | 4/2005 | Nichols et al. ................. 606/914 |
| 6,887,241 B1 * | 5/2005 | McBride et al. ............. 606/86 A |
| 7,137,986 B2 * | 11/2006 | Troxell et al. ................. 606/252 |
| 7,201,530 B2 * | 4/2007 | Wappes et al. .................. 403/27 |
| 7,488,005 B2 * | 2/2009 | Gunderson .................... 285/319 |
| 7,604,654 B2 * | 10/2009 | Fallin et al. .................... 606/258 |
| 7,628,799 B2 * | 12/2009 | Richelsoph et al. ........... 606/250 |
| 7,955,363 B2 * | 6/2011 | Richelsoph .................... 606/305 |
| 8,118,837 B2 * | 2/2012 | Lemoine ....................... 606/246 |
| 2003/0028192 A1 | 2/2003 | Schar |
| 2005/0203514 A1 * | 9/2005 | Jahng et al. ..................... 606/61 |
| 2006/0064090 A1 * | 3/2006 | Park ................................. 606/61 |
| 2006/0189983 A1 * | 8/2006 | Fallin et al. ..................... 606/61 |
| 2006/0229612 A1 * | 10/2006 | Rothman et al. ............... 606/61 |
| 2006/0271051 A1 * | 11/2006 | Berrevoets et al. ............ 606/61 |
| 2007/0049932 A1 * | 3/2007 | Richelsoph et al. ............ 606/61 |
| 2007/0270816 A1 * | 11/2007 | Rezach ............................ 606/61 |
| 2007/0270972 A1 * | 11/2007 | Gordon et al. ............. 623/17.16 |
| 2008/0015584 A1 * | 1/2008 | Richelsoph .................... 606/61 |
| 2010/0094345 A1 * | 4/2010 | Saidha et al. ................. 606/250 |

FOREIGN PATENT DOCUMENTS

| | | |
|---|---|---|
| EP | 0578320 A1 | 1/1994 |
| EP | 1762195 A1 | 3/2007 |
| WO | WO 99/09901 | 3/1999 |

* cited by examiner

*Primary Examiner* — Daniel P Stodola
*Assistant Examiner* — Jonathan Masinick
(74) *Attorney, Agent, or Firm* — Kohn & Associates, PLLC

(57) ABSTRACT

A rod to rod connector includes a connector body containing a rod retaining insert. An interconnecting portion inner connects to a body to at least one other connector body. The insert is snap locked within the connector body simultaneously while retaining a rod within the insert in a locked condition.

22 Claims, 10 Drawing Sheets

ROD TO ROD CONNECTOR WITH LOAD SHARING

TECHNICAL FIELD

The present invention relates to transverse connectors which generally include a pair of coupler bodies, each of the coupler bodies including a connecting mechanism for connecting each coupler body to a spinal rod for the purpose of interconnecting a pair of spinal rods. The present invention is a cervical tool or medical construct used with spinal rods for the purpose of spinal fixation and correction of spinal curve.

BACKGROUND OF THE INVENTION

Spinal rods are used for spinal fixation operations, often times for correction of scoliotic curves. Fixation using such rods often involves the use of plates and/or screws for retaining the rods and operative connection with the spine. Usually, a pair of rods are placed on opposite sides of the portion of the spine to be fixed. Various systems, usually transverse connectors, have been developed for cross linking spinal rods to prevent rod migration and to increase stiffness of the paired rod assembly. Such connectors are used in corrective operations where the rod is rotated to correct spinal curvature. The transverse connectors can be use to further stabilize the rod to rod positions.

Many assemblies used for interconnecting spinal rods, referred to as transverse connecting assemblies or rod to rod couplers, utilize a plate mechanism having connectors for adjustably retaining hook systems that are bolted in place in the plate. Examples of such systems are U.S. Pat. No. 5,334,203 to Wagner, issued Aug. 2, 1994, and U.S. Pat. No. 5,522,816 to Dinello, et al. issued Jun. 4, 1996. The U.S. Pat. No. 5,498,263 to Dinello, et al. issued Mar. 12, 1996, discloses a transverse connector system utilizing set screws to interconnect vertebrae coupling members while using plate members as described above for interconnecting the coupling members such that a squared unit is formed having two sides defined by the plate member and two sides defined by the spaced rod members.

U.S. Pat. No. 5,312,405 to Korotko, et al. issued May 17, 1995 discloses a coupler used for interconnecting spinal rods where the coupler itself is a two piece unit, the neck portion of each unit being interconnected by a screw mechanism which clamps a male portion within a female portion of the system. This system also utilizes couple inserts or yokes which engage a rod. The rod is disposed within a seat portion of each coupler and compressed by an instrument which engages the bottom of the rod between the rod and the spine and the top of the coupler. U.S. Pat. No. 5,275,600 to Allard, issued Jan. 4, 1994, discloses a telescoping rod to rod coupler wherein the connector bodies are interconnected by a telescoping mechanism which varies the distance between the coupled bodies. A telescoping connection is also disclosed in the U.S. Pat. No. 6,328,741 to Richelsoph, issued Dec. 11, 2001.

The U.S. Pat. Nos. 6,171,311 and 6,328,740, both to Richelsoph, issued Dec. 11, 2001, and Jan. 9, 2001, respectively, each disclose a transverse connector including a pair of transverse connector bodies and connector inserts for connecting a rod to each of the transverse connector bodies. Both patents disclose inserts including threaded neck portions for being connected by a connector through an opening in the base portion of the connector bodies. A locking and fixing mechanism draws the inserts into seat portions of the transverse connector bodies while simultaneously locking the transverse connector inserts in the insert seat portions and compressing the rods seat surface of the insert to lock a rod within the seats. More specifically, a neck member engages and locks the insert within an insert seat. In order to affect the locking mechanism, the surgeon must use a threaded nut to engage threads on the insert member to draw it into the connector body and lock the assembly on the spinal rod.

It would be desirable to be able to securely hold and lock an insert, retaining a rod therein, in the locked position without threads, nuts, set screws, or other hardware. Further, it is desirable to provide a mechanism for sharing loads between the connector body portions without increasing the height of the profile of the insert while controlling rigidity and allowing load sharing.

SUMMARY OF THE INVENTION

In accordance with the present invention, there is provided a rod to rod connector including a connector body containing a rod retaining insert, an interconnecting mechanism for interconnecting the connector body to at least one other connector body, and a snap lock for snapping the insert into a locked condition simultaneously relative to the connector body and about a rod retained within the insert.

The present invention further provides a rod connector insert including the snap locking mechanism for snapping the insert within a locked condition simultaneously relative to a connector body and about a rod contained within the insert.

The present invention further provides a rod connector insert including the snap locking mechanism for snap locking the insert into a connector body in a snap locked condition and a compression mechanism for compressing a rod seat of the insert allowing the rod while simultaneously in the snap lock condition.

The present invention further provides a method of interconnecting two rods by seating a rod in a rod seat of an insert which is seated within a connector body in a rod to rod connector and simultaneously snap locking the insert into the connector body while compressing the rod seat about the rod seated therein.

Additionally, the present invention provides a method of locking a rod within an insert member by simultaneously snap locking the insert into a connector body while compressing a rod seat of the insert member about a rod.

DETAILED DESCRIPTION OF THE INVENTION

Figure 1:
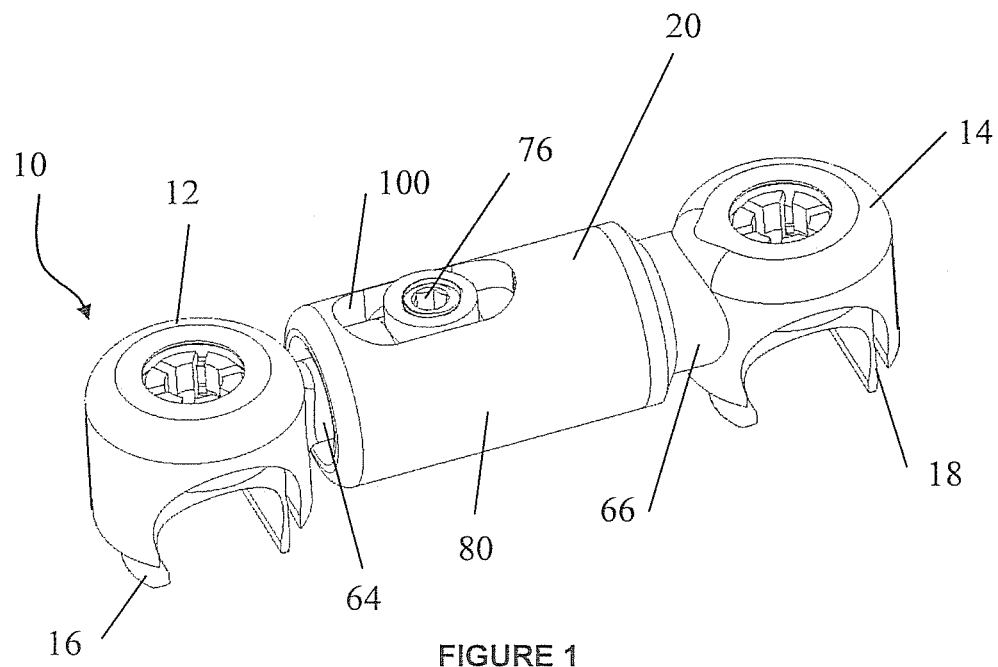
FIG. 1 is a perspective view of the inventive rod to rod connector of the present invention.
Figure 2:
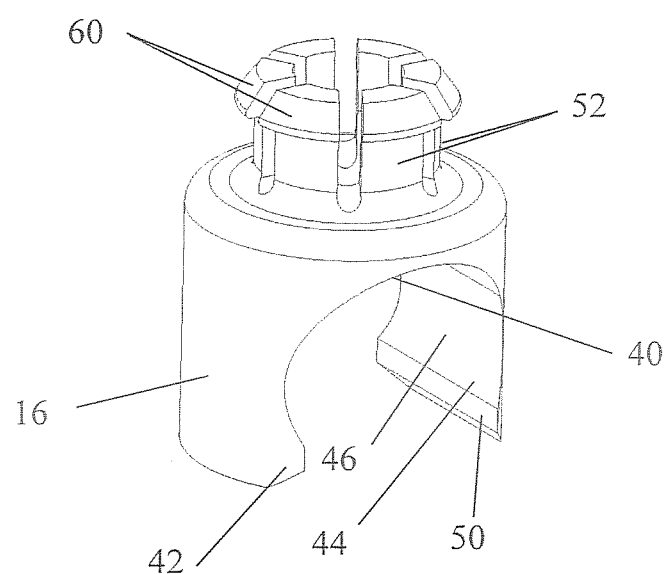
FIG. 2 is a perspective elevational view of an insert member of the present invention.
Figure 3:
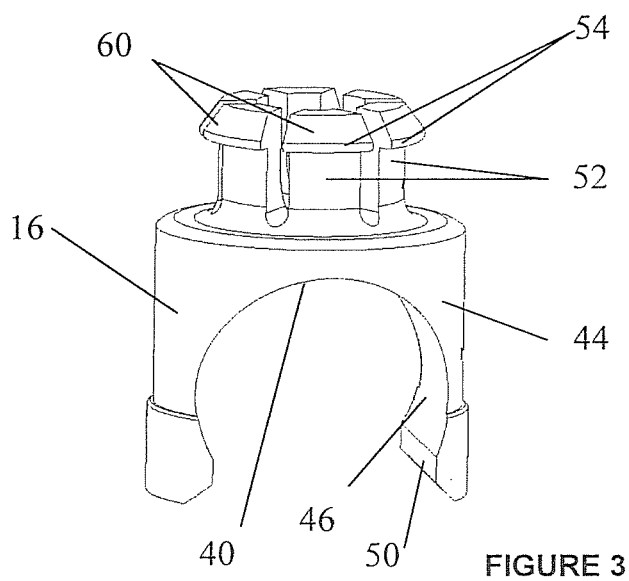
FIG. 3 is an elevational perspective view of the insert member.

A rod to rod connector made in accordance with the present invention is generally show at 10 in the figures. Rod to rod connectors are also referred to in the art as transverse connectors. Generally, the rod to rod connector 10 includes a pair of connector bodies 12, 14, each containing a rod retaining insert generally indicated at 16, 18. The connector 10 further includes an interconnector mechanism generally indicated at 20 for interconnecting the connector bodies 12, 14 to each other. The connector 10 further includes a snap lock mechanism for snapping the inserts 16, 18 into a locked condition simultaneously relative to the connector bodies 12, 14 and about a rod 22, 24 retained within each insert 16, 18. The snap lock mechanism requires a single hand of a practitioner or a single tool having a clamping mechanism to force each insert 16, 18 into a locked condition within each of the connector bodies 12, 14, the single motion resulting in the simultaneous locking of the insert 16, 18 within the connector body 12, 14 and locking and secure retention of a rod 22 therein. Thus, the present invention provides a means of locking a rod 22 within a connector body 12, 14 without threads, nuts, set screws, or other hardware. Such a locking mechanism is useful in a rod to rod connector as well as in other rod retaining orthopedic devices.

Figure 4:
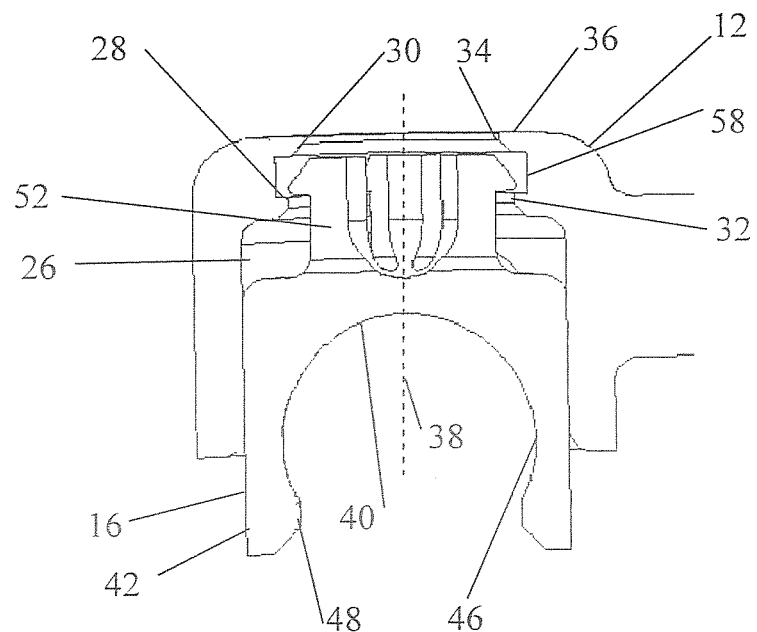
FIG. 4 is an elevational view in cross section of the insert member seated within a connector body.
Figure 5:
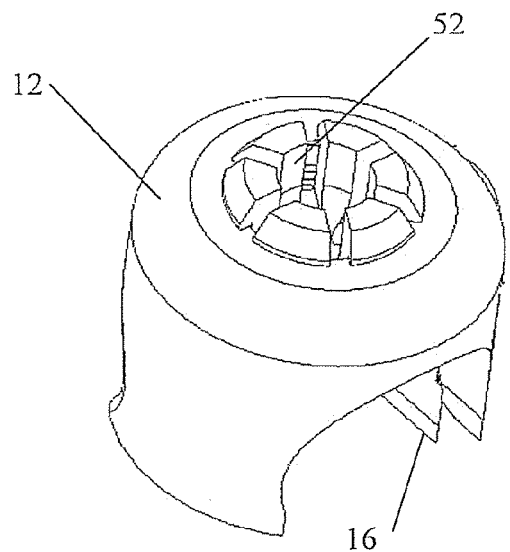
FIG. 5 is perspective view of an insert member in the locked condition seated within the connector body.

More specifically referring to FIG. 4, each connector body 12, 14 (FIG. 4 showing only connector body 12) includes an inner cup shaped portion defined by an annular wall 26 and a base portion 28. The base portion includes an opening 30 extending there through. In cross section, the base portion 28 includes a first radially inwardly extending flange 32, adjacent the cup shaped surface and a second radially inwardly extending flange 34, adjacent the outer surface 36 of the connector body. The wall 26 of the connector body can have a substantially flat surface and cross section as shown in FIG. 4 or can be frusto-conical having a portion closer to the base portion 28 of a smaller diameter to compress the insert 16 when drawn into the cup shaped portion for reasons discussed below. In other words, the cup shaped inner surface 28 includes the base portion 28 integrally connected to the substantially annular side wall 26 defining a central axis shown as hatched line 38. The side wall 26, as shown in FIG. 4, is spaced from and about the central axis, the insert 16 being seated within the cup shaped inner surface.

As best shown if FIGS. 2-5, the insert includes a base portion 40 and spaced flexible arm portions 42, 44 extending therefrom. The base portion 40 and arms 42, 44 combine to define a substantially u-shaped inner surface 46, the u-shaped inner surface defining a rod seat 46. As best shown in FIG. 4, the substantially u-shaped inner surface or rod seat 46 can include radially inwardly projecting portions 48, 50 for partially wrapping around and releasably retaining a rod 22 therein.

In one embodiment of the present invention, the wall portion 26 of the cup shaped inner surface can be substantially flat and annular while the outer surface of the insert 16 can have a radially outwardly extending step portion. Accordingly, as the insert 16 is forced into the cup shaped inner surface, the flexible arms 42, 44 of the insert 16 are compressed radially inwardly. If a rod 22 is seated within the substantially u-shaped inner surface 46 of the insert, and the insert is forced into the cup shaped portion of the connector body 12, then the flexible arms 42, 44 of the insert 16 are forced inwardly to engaging contact with the rod 22 seated therein for securely retaining the rod within the connector body 12.

The snap locking mechanism of the present invention is best illustrated in FIGS. 2-5. The snap locking mechanism includes a slotted neck portion 52 extending from the base portion 40 of the insert 16 in a direction along the axis 38 opposite to the rod seat 46. The slotted neck portion 52 includes a plurality of fingers defining the neck portion 52, each finger including the radially outwardly extending flange portion 54 defining a gripping mechanism for gripping surface of the cup shaped portion to lock the insert 16 within the cup shaped portion while simultaneously the cup shaped portion compresses the flexible arms 42, 44 of the about a rod 22 seated in the rod seat 46. More specifically, the annular flanges 30, 32 extending radially inwardly about the opening through the base portion of the connector bodies 12, 14 define a capture channel or pocket 58, as best shown in FIG. 4. The rod to rod connector 10 of the present invention has an unlocked condition wherein the outwardly extending flange 54 is captured within the capture channel 58 and retained therein by the flanges 54 being captured between inwardly extending flanges 32 and 34. This condition is best illustrated in FIGS. 1, 4, 7, and 8. Thus, the flanges 54 grip the inner inwardly radially extending flange 32 thereby maintaining the insert 16 in a condition for easily receiving a rod 22 by snapping the rod past the projections 48, 50 on the inner surface 46 of the insert 16 for retention within the rod seat 46. In this condition, the rod can easily be snapped into the rod seat 46 or out of the rod seat 46 for adjustment. Likewise, once snapped into the rod seat 46, the rod is not necessarily locked in place but the device can be retained on the rod for actual adjustment along the length of the rod or for removal from the rod in its entirety. In this condition, the flexible arms 42, 44 of the insert 16 are not compressed about the rod 22 but the insert has sufficient rigidity to be retained on the rod.

The neck portion 52 is of sufficient length such that when the insert member 16 is forced into the cup shaped portion of the connector body 12, the flanges 54 can be compressed inwardly so that the entire flange portion including flanges 54 is forced through the entire opening 30, through the radially inwardly extending flange portion 34 such that the gripping flanges 54 clip an outer surface about the opening 30 of the connector bodies thereby snap locking the insert member 16 to a locked condition. In other words, the neck portion 52 is movable through the opening 30 to allow the insert 16 to be drawn further and totally into the cup shaped pocket. Each of the flanges 54 can have a tapered surface 60 to facilitate the ease of insertion of the neck portion 52 and adjacent flanges 54 through the inwardly extending first flange 32 and eventually placing the insert 16 in the locked condition by forcing the flanges 54 through the second inwardly extending flange portion 34. Each of the flange portions 32 and 34 can have curved surfaces that also facilitate ease of insertion. However, the flange 34 will generally extend radially inwardly further than the flange 32 in order to facilitate the ease of placing the flanges 54 into the capture channel 58 and preventing the neck portion 52 from too easily passing through the second opening 30 so as to inadvertently insert member 16 into a locked condition. In other words, it takes greater effort to place the assembly in the locked position, which is preferable. The finger-like projections defining the neck portion 52 have to be sufficiently flexible to allow the insert 16 to be moved from the unlocked to the locked condition while being sufficiently rigid to maintain the gripping function of the flanges 54 vis-à-vis the first and second radially inwardly extending flanges 32, 34. The insert member 16 shown in the locked condition in FIGS. 5, 6, 14-16, 17, 19, and 20.

What is evident from the above is that forcing the insert member 16 into the cup shaped inner surface of the connector body 12 simultaneously locks the insert therein while compressing the arms 42, 44 about a rod member 22 seated therein in a locked condition. That is, the inserts are locked in place and the rods securely locked within the rod seat of the insert member 16. A surgeon can perform this function with a single motion with a single hand or by use of a clamp-type instrument, all within a single motion and all without manipulation of any other hardware. Since the interference of the projections 48, 50 retain the rod member within the rod seat of the insert 16, this interference in combination with the outside of the insert being compressed within the cup shaped pocket creates the force to hold the rod in a locked condition, as the flanges 54 gripping the outer surface above the opening 30 prevents the insert from moving back out of the cup shaped inner surface. It must be emphasized that this locked condition is maintained without the use of threads, nuts, set screws, or other hardware.

The connector bodies are preferably formed of materials well known in the art for such uses, such as implant grade titanium or titanium alloys, stainless steel or other sufficiently strong metals or polymers. All the materials are contemplated, provided material is strong enough to endure the high loads transmitted through such components.

The insert member can be made from titanium or titanium alloys, stainless steels, or polymers of sufficient strength, such as PEEK.

In one embodiment of the present invention, the connector bodies 12, 14 can be interconnected at a fixed distance by solid interconnecting portion. Alternatively, and preferably, the interconnecting portion 20 can include a mechanism for varying the length so as to suggest a length of the inner connection portion 20 and space the connector bodies apart in a preferred distance. U.S. Pat. No. 3,632,8741 to Richelsoph, issued Dec. 11, 2001 shows one type of length variable interconnecting portion. The present invention combines a length variable portion (made by various means to be discussed below) with a further mechanism for sharing loads between the connector bodies 12, 14. The loads are shared while the interconnecting portion 20 contributes to the rigidity of the rod to rod connector 10, as described in detail below.

Figure 6:
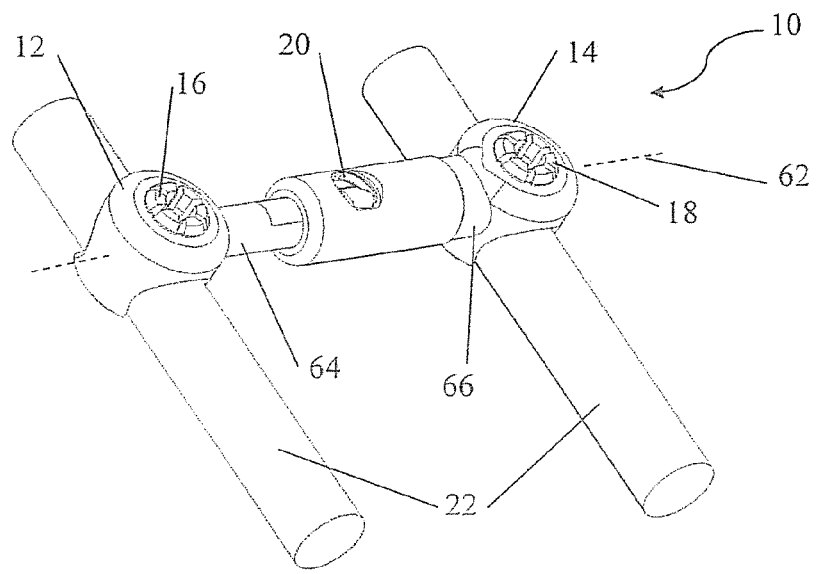
FIG. 6 is a perspective view of a pair of rods that are connected by a transverse connector of the present invention in a locked condition.
Figure 7:
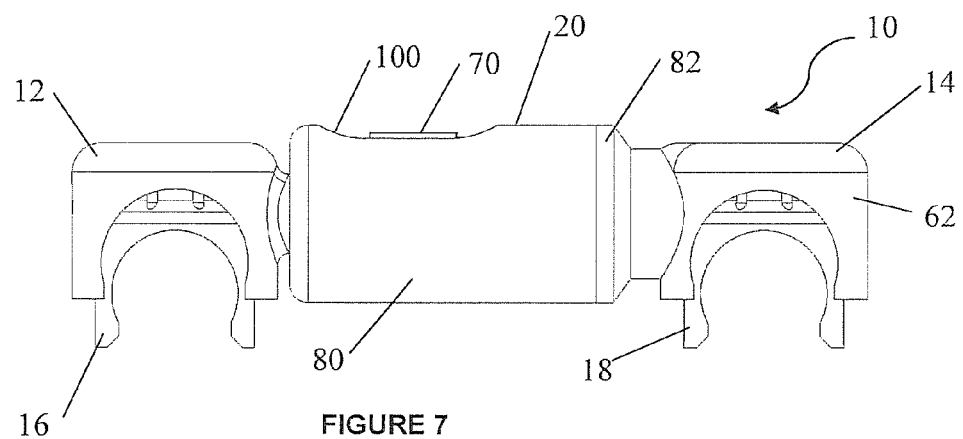
FIG. 7 is a side elevational view of the present invention wherein the insert members are in an unlocked condition.
Figure 8:
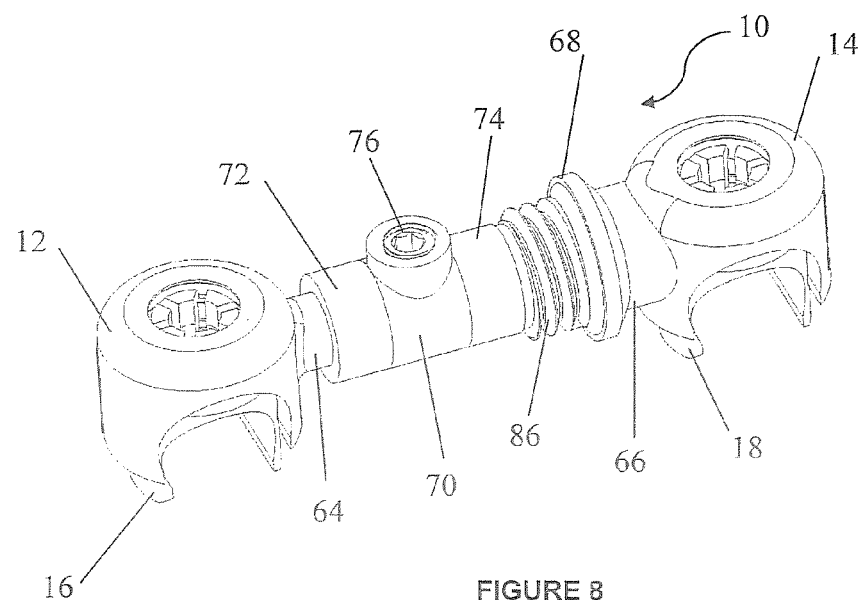
FIG. 8 is a perspective top view of the present invention with an external body member removed to reveal the load sharing mechanism of the present invention.

In the preferred embodiment, the interconnecting portion 20 includes a telescoping mechanism for allowing adjustment of the distance between the connector bodies 12, 14. This telescoping mechanism allows for linear movement substantially along an axis 62 as best shown in FIGS. 6 and 7. The telescoping mechanism also includes a locking mechanism for locking the telescoping interconnecting portion 20 at a fixed length, the load sharing mechanism being operatively connected between the telescoping connector mechanism and the locking mechanism as discussed below.

More specifically, the telescoping mechanism includes a forced tubular portion 64 extending from one of the connector bodies 12 and a socket portion 66. The socket portion includes a radially outwardly extending abutment 68 as best shown in FIGS. 8, 9, 14, and 15. The locking mechanism includes a locking positional ring 70 as shown in FIGS. 8, 9, 11, and 16-18. The elastomeric rings 72 and 74, comprising the load sharing mechanism, seated on the tubular portion 64 on each side of the locking positional ring 70. The locking member 70 includes a set screw 76 disposed therein for locking engagement with the tubular portion 64 for locking positional ring 70 and elastomeric rings 72, 74 at a previously determined position along the length of the tubular portion 64. An external body 80 includes a first end 82 having a threaded inner surface 84 which threadingly engages a threaded portion 86 on the socket portion 66. The external body 80 has a second end portion 88 having a radially inwardly extending flange 90 which abuts against an outer surface 92 of the elastomeric ring 72. Thus, when assembled together, the external body 80 draws the tubular portion 64 into the socket portion 66. The extent that the tubular portion 64 is disposed into the socket portion 66 is determined by the position of the locking member 70 as it is locked on to the tubular portion 66 by set screw 76. Once the set screw fixes the position of the locking positional ring 70, the tubular portion 64 is inserted into the socket portion 66 until an end portion 94 of the elastomeric ring 74 abuts against an end portion 96 of the threaded portion 86. By threading the external body onto the socket portion 66 and the external body abutting against and engaging the elastomeric ring 72 which abuts against the locking positional ring 70, the entire assembly is secured together. In this condition, a dynamic load sharing system is created for the rod to rod connector 10 to be able to contribute to the system rigidity without compromising load sharing. That is, the two connector bodies 12, 14 and inserts 16, 18 become a load sharing mechanism.

Figure 9:
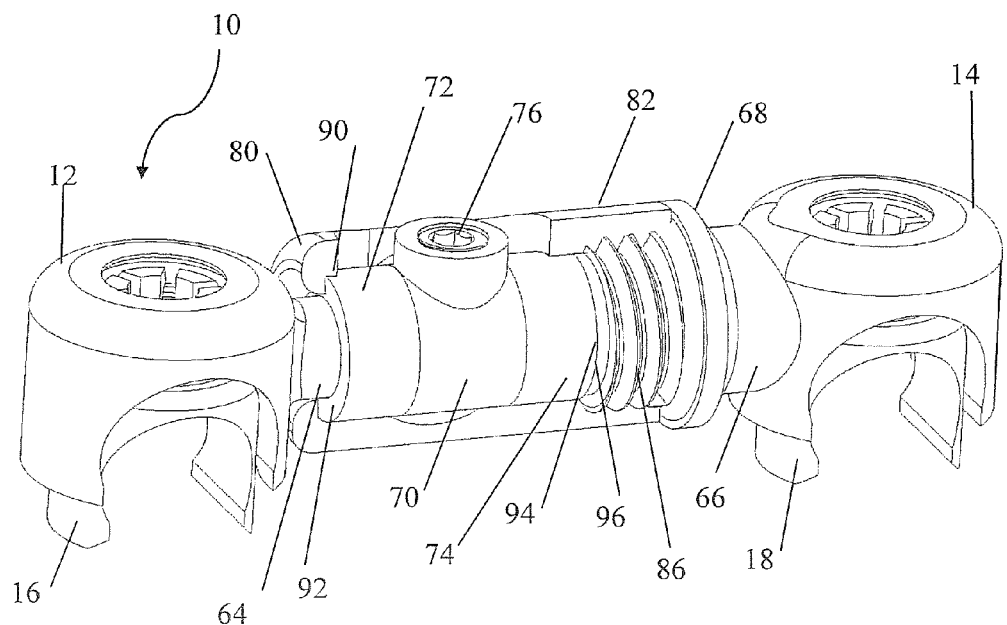
FIG. 9 is an elevational perspective view partially broken away showing the load sharing mechanism within the external body member of the present invention.
Figure 10:
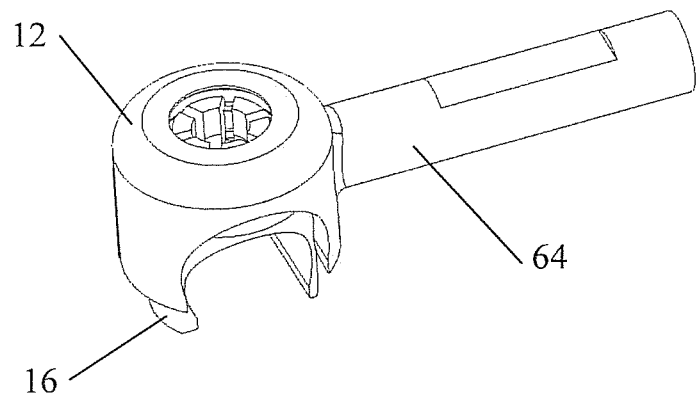
FIG. 10 is a side perspective view of one of the connector bodies of the present invention having a tubular portion extending therefrom.
Figure 11:
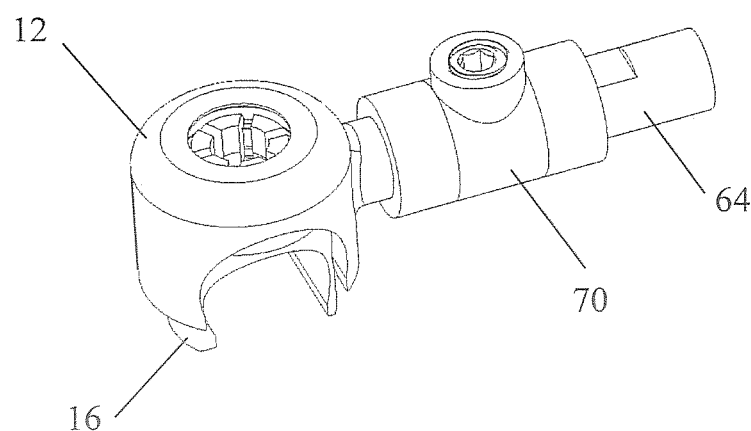
FIG. 11 is a view similar to FIG. 10 showing the load sharing members mounted on the tubular portion about a locking member.

The load sharing mechanism is accomplished as the inner connection between the connector bodies is through the elastomeric rings. A tubular portion 64 slides within the external body 82 and is suspended away from the walls by the elastomeric rings 72, 74. As best shown in FIG. 9, the locking positional ring 70 is locked to the tubular portion 64. The only way the tubular portion 64 can move is by compression of the elastomeric rings 72, 74, as the rings are trapped between the faces of the external body 82 and the faces of the socket portion 66. The allowed motion can be linear, depending on diameter of through hole of the socket portion 66 which the tubular portion 64 passes through. The motion can also be three dimensional if the hole in the socket portion 66 is larger than the diameter of the tubular portion 64.

This instruction is desirable in that prior art polyaxial screws have allowed load sharing, which is restricted motion. In the spine, there are usually two rods, one on either side of the spine. It is possible utilizing the present invention that load sharing will be slightly uneven from side to side. When connected by the rod to rod connector 10 of the present invention, if the connector 10 is rigid, the connector 10 distributes the unbalanced load to the other side and potentially defeat the efforts of load sharing by holding the other side rod from properly loading the graft. By allowing controlled load sharing in the connector 10 of the present invention, the connector 10 still provides rigidity to the construct while distributing loads more evenly.

The elastomeric rings can be made from various materials well known in the art, and can be flexible or semi-flexible materials, or spring-like materials. Moreover, the rings can be of a dual durometer depending on the pre-load and operational loading capabilities. Examples of such materials are silicone, polyurethane, polycarbonate-urethane, PEEK, polyethylene, and other suitable materials.

Figure 12:
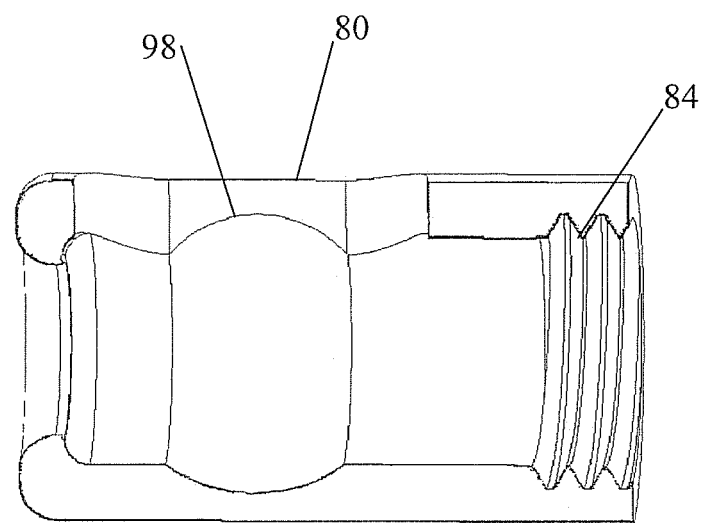
FIG. 12 is side view in cross section of the external body member.
Figure 13:
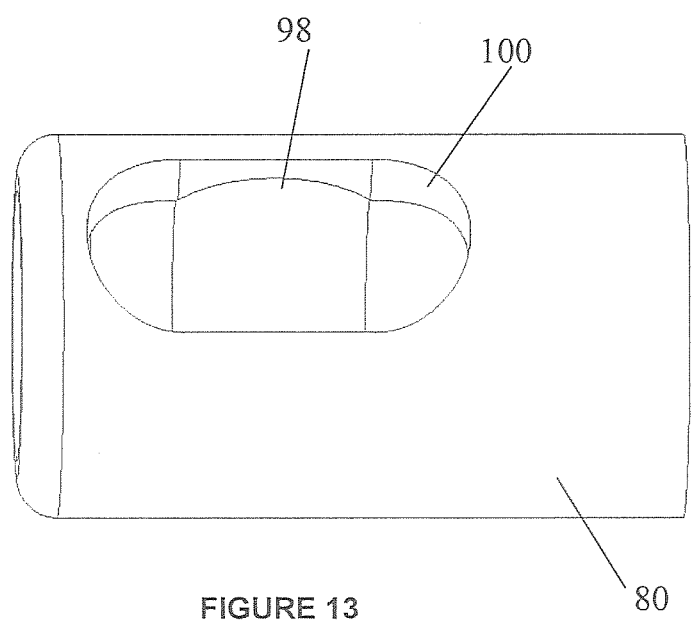
FIG. 13 is a top elevational view of the tubular portion extending from one connector body invading engagement with the socket portion of a second connector body.
Figure 14:
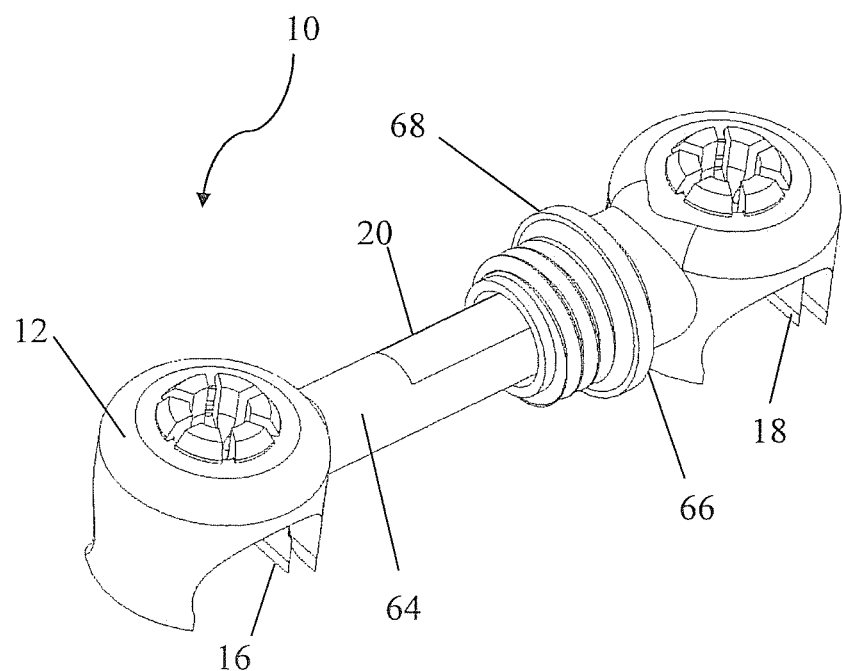
FIG. 14 a perspective view of the invention.

As shown in FIGS. 12 and 13, the external body 80 includes as recessed pocket portion 98 on the inside surface thereof. The recessed pocket 98 allows the locking positional ring 70 to drop and turn 90 degrees, allowing for the threading engagement of the external body 80 onto the threaded portion 86. The actual body member also includes an opening 100 to allow for the locking positional ring 70 to be disposed therein.

It should be noted that the external body 70 can be connected to the socket portion 66 by various means other than by threads. For example, it can be pressed or pinned or both or other locking mechanisms.

Figure 15:
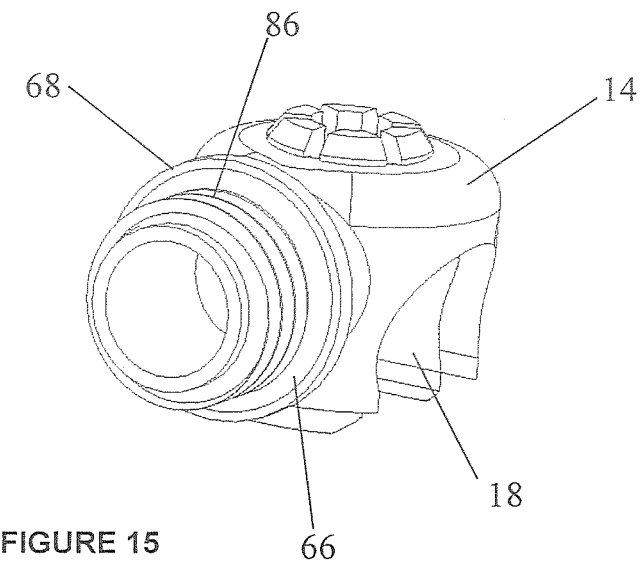
FIG. 15 is an end on perspective view of the connector body including the socket portion.

As shown in FIG. 15, the socket portion 66 can be bored to allow the tubular portion 64 to slide within it, thereby increasing the length of useable shaft. As stated before, the locking positional ring can be locked along a length of the tubular portion 64 to adjust that length in a fixed position.

Figure 16:
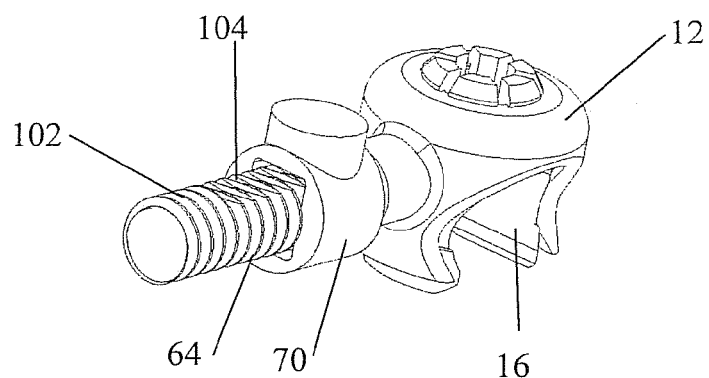
FIG. 16 is an end on perspective view of the connector body having the tubular portion and including the locking member mounted on the tubular portion.
Figure 17:
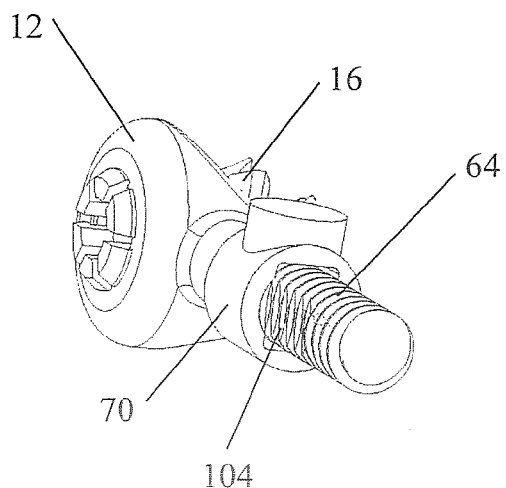
FIG. 17 is an end on perspective view of the assembly show in FIG. 16 with the locking member rotated 90 degrees relative to the connector body.
Figure 18:
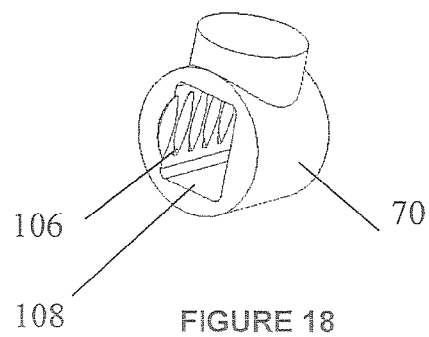
FIG. 18 is an end on perspective view of the locking mechanism.

FIGS. 16-18 show an alternative embodiment for positioning the locking positional ring 70. As shown in FIGS. 16 and 17, the tubular portion 64 can have a threaded outer surface 102 having a flat portion 104. Threads are removed at the flat portion. The locking positional ring includes a threaded inner surface 106, as best show in FIG. 18 with part of the thread machined away as shown at 108. By rotating the tubular portion 64 90 degrees, the threads are disengaged from the locking positional ring thereby allowing the locking positional ring 70 to freely slide along the tubular portion 64. Upon turning the shaft back 90 degrees, the threads reengage locking the distance between the ends. This results in an easy quick positioning locking mechanism.

Figure 19:
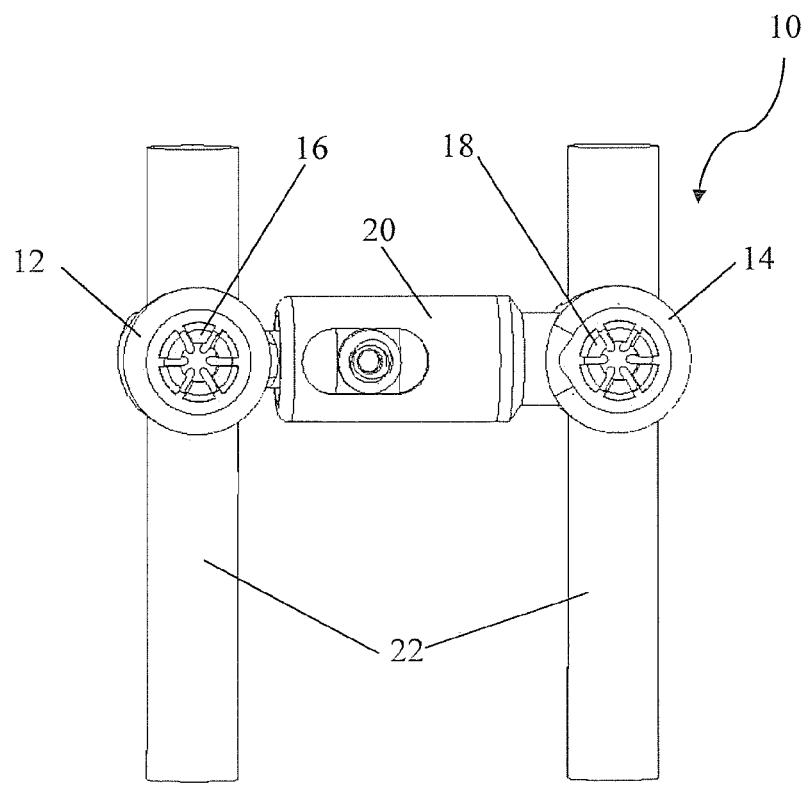
FIG. 19 is a top plan view of the assembly of the present invention interconnecting two rods.
Figure 20:
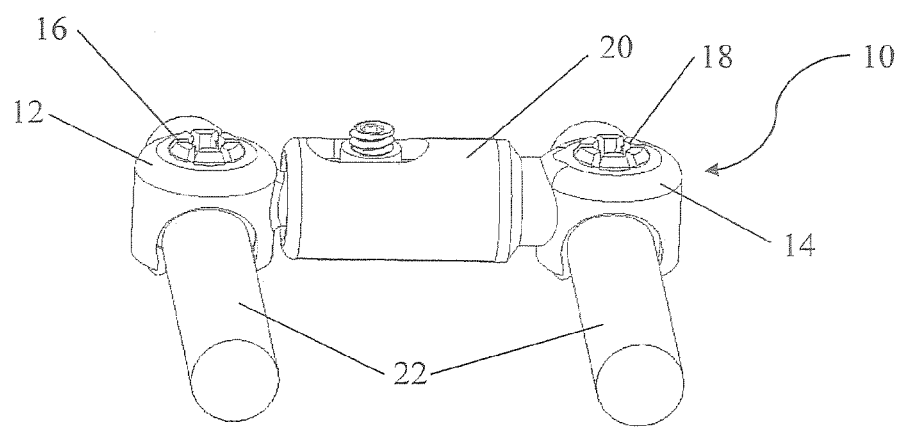
FIG. 20 is a side oriented perspective view of the present invention interconnecting the two rod members.

In operation, two rods 22 are inner connected by seating the rod 22 in a rod seat of an insert 16 which is seated within a connector body 12, 14 and simultaneously snap locked into the connector body 12, 14 while the rod seat is compressed around the rod 22 seated therein. More specifically, the assembly as shown in FIG. 1 is broadened proximity of a pair of spaced rods 22 the rods are usually inner connected to vertebrae by various types of screws known in the art. The rods are disposed within the rod seats of the inserts 16, 18. The connector bodies 12, 14 are brought into preferred proximity and locked relative to each other by timing that of the said screw 76. Thus, the load sharing elastomeric rings 72, 74 are connected between the otherwise moveable connector bodies 12, 14 thereby absorbing loads between the connector bodies 12, 14. That is, the connector bodies 12, 14 are inner connected through what could be considered a suspension mechanism assigned by the elastomeric rings 72, 74. Once property positioned, the inserts 16, 18 containing rod members 22 therein, as shown in FIGS. 19 and 20 are forced from the unlocked condition into the locked condition by being forced into the connector bodies such that the flange portions 6 engage an outer surface about the opening 30 in the connector bodies 12, 14. Thus, the inserts 16, 18 are in the locked condition so that they cannot be released there from while the rods 22 are simultaneously in a locked retained condition within the connector bodies 12, 14. Thus, the present invention provides a snap lock mechanism for snapping the inserts 16, 18 into a locked condition simultaneously relative to the connector bodies 12, 14 and about the rods 22 retained within the inserts 16, 18. Moreover, the present invention provides a method of interconnecting two rods by seating a rod in a rod seat of an insert 16, 18 which is seated within a connector body 12, 14 and simultaneously snap locking the insert 16 into the connector body 12, 14 while compressing the rod seat about the rod 22 seated therein. Moreover, the present invention involves a method of locking a rod 22 within an insert 16 by simultaneously snap locking the insert 16 into a connector body 12, 14 while compressing a rod seat of the insert 16 about the rod 22.

What is claimed:

1. A rod to rod connector comprising:
a connector body containing a rod retaining insert;
an interconnector mechanism for interconnecting said connector body to at least one other connector body; said insert including spaced flexible arm portions extending from a base of said insert having a combined substantially u-shaped inner surface defining a rod seat and having a compressible outer surface for compressing about and locking a rod seated within said insert in combination with a separate flexible outwardly flanged portion of said base of said insert for snap fitting engagement with a base portion of said connector body, whereby said insert is movable into a locked condition within said connector body by a single clamping mechanism by locking engagement between said flexible outwardly flanged portion and a cup shaped inner surface of said connector body while simultaneously locking said arms of said insert about a rod retained within said rod seat in a single motion, wherein said connector body includes an annular wall and wherein said outer surface of said insert includes a portion that is larger relative to said annular wall, whereby insertion of said insert into said connector body results in said annular wall compressing against said outer surface of said insert and results in said flexible arms being compressed into locking engagement about said rod while said insert is simultaneously locked in said connector body.

2. The connector of claim 1 wherein said cup shaped inner surface includes a base portion integrally connected to a substantially annular side wall defining a central axis extending through said base portion, said side wall being annularly spaced from and about said central axis, said insert being seated within said cup shaped inner surface.

3. The connector of claim 2 including snap locking means having a slotted portion extending from said base portion in a direction along said axis opposite to said rod seat, said slotted portion including gripping means for gripping a surface of said cup shaped portion to lock said insert within said cup shaped portion while simultaneously said cup shaped portion compresses said arm portions about a rod seated in said rod seat.

4. The connector of claim 3 wherein said base portion of said cup shaped inner surface includes an opening therethrough, wherein said gripping means engages said base of said cup shaped inner surface about said opening.

5. The connector of claim 4 wherein said base portion of said cup shaped inner surface includes a first substantially annular flange about said opening adjacent an outer surface of said connector body and a second substantially annular flange spaced from said first flange and defining a captive channel therebetween, said gripping means being returned in said captive channel when said insert is in an unlocked condition wherein said insert is retained in said connector body and uncompressed.

6. The connector of claim 5 wherein said gripping means includes a neck portion and radially outwardly extending flanged portions, said neck portion extending through said second flange about said opening and said radially outwardly extending flange being captured in said capture channel where said insert is in said unlocked condition, said insert being moveable through said opening to snap lock said outwardly extending flange over said first inwardly extending flange wherein said insert is in said locked condition.

7. The connector of claim 6 wherein said arm portions include a radially outwardly projecting portion on said outer surface thereof proximate to said arm portions distal relative to said base portion, said outwardly projecting portion being outside of said cup shaped portion when said insert is in said unlocked condition and adjacent to and compressed by said annular wall of said cup shaped portion when said insert is in said locked condition for gripping and seated in said rod seat.

8. The connector of claim 7 wherein said arms defining said rod seat are radially inwardly and outwardly flexible and define a substantially cup shape of said rod seat for being gripped substantially around a portion of a rod seated therein said unlocked condition and securely compressing inward and retaining the rod seated in said rod seat in said locked condition.

9. The connector of claim 1 wherein said connector includes two connector bodies, said interconnector mechanism includes a tubular portion fixedly interconnecting said two connector bodies.

10. The connector of claim 1 wherein said interconnector mechanism includes length variation means for adjusting a length of said interconnecting mechanism and spacing of said connector bodies.

11. The connector of claim 1 wherein said interconnector mechanism includes load sharing means for sharing loads between said connector bodies while contributing to rigidity of said connector.

12. The connector of claim 11 wherein said tubular portion defines a longitudinal axis of said interconnector mechanism, said interconnector mechanism further including telescoping connector means telescopically interconnecting said connector bodies for linear movement substantially along said longitudinal axis relative to each other and locking means for locking said telescoping connector means at a fixed length, said load sharing means being operatively connected between said telescoping connector means.

13. The connector of claim 12 wherein said connector includes two connector bodies, said telescoping connector means includes a tubular portion extending from one of said connector bodies and a socket portion extending from another of said connector bodies.

14. The connector of claim 13 wherein said socket portion includes first engagement means for fixedly engaging a first end of said locking means, said tubular portion including second engagement means for fixedly engaging a second end of said locking means, said locking means containing said load sharing means therebetween.

15. The connector of claim 14 said locking means includes an external body member disposed over said telescoping connector means, said external body member including a first end including said first engagement means and a second end including said second engagement means.

16. The connector of claim 15 wherein said first end of said external body member includes a threaded portion for threaded engagement with a threaded outer surface of said socket portion thereby defining said first engagement means.

17. The connector of claim 15 wherein said second end of said external body member includes a radially inwardly extending flange relative to said longitudinal axis, said flange engaging a shoulder of said load sharing means, said load sharing means being fixed secured to said tubular portion extending from said connector body, said flange and shoulder combines to define said second engagement means.

18. The connector of claim 17 including locking positional means for locking said load sharing means at a predetermined position along said tubular portion extending from said connector body.

19. The connector of claim 18 wherein said locking positional means includes a ring member and a second locking means for locking said ring member along a length of said tubular portion extending from said connector body.

20. The connector of claim 19 wherein said load sharing means includes a first load sharing member in engagement between said ring member and an end portion of said socket portion and a second load sharing member in engagement between said ring member and said radially inwardly external flange of said external body member.

21. The connector of claim 20 wherein said load sharing members are ring shaped and each disposed about said tubular portions extending from said connector bodies.

22. The connector of claim 21 wherein said load sharing members are made from a material selected from the group including silicone, polyurethane, polycarbonate-urethane, PEEK, and polyethylene.

* * * * *